United States Patent
Baran et al.

(10) Patent No.: US 10,676,481 B2
(45) Date of Patent: Jun. 9, 2020

(54) INTERMEDIATES IN THE SYNTHESIS OF ERIBULIN AND RELATED METHODS OF SYNTHESIS

(71) Applicant: EISAI R&D MANAGEMENT CO., LTD., Tokyo (JP)

(72) Inventors: Phil S. Baran, San Diego, CA (US); Charles E. Chase, Londonderry, NH (US); Francis G. Fang, Andover, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 45 days.

(21) Appl. No.: 16/076,028

(22) PCT Filed: Feb. 10, 2017

(86) PCT No.: PCT/US2017/017501
§ 371 (c)(1),
(2) Date: Aug. 7, 2018

(87) PCT Pub. No.: WO2017/139664
PCT Pub. Date: Aug. 17, 2017

(65) Prior Publication Data
US 2019/0300542 A1   Oct. 3, 2019

Related U.S. Application Data

(60) Provisional application No. 62/294,538, filed on Feb. 12, 2016.

(51) Int. Cl.
C07D 493/00 (2006.01)
C07D 493/22 (2006.01)

(52) U.S. Cl.
CPC .................. *C07D 493/22* (2013.01)

(58) Field of Classification Search
CPC ...... C07D 493/22; A61K 31/357; A61P 35/00
USPC .................................................. 549/348, 351
See application file for complete search history.

(56) References Cited

U.S. PATENT DOCUMENTS

| | | |
|---|---|---|
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,148,554 B2 | 4/2012 | Seletsky et al. |

(Continued)

FOREIGN PATENT DOCUMENTS

| | | |
|---|---|---|
| EP | 0572109 A1 | 12/1993 |
| JP | 2010-168320 A | 8/2010 |

(Continued)

OTHER PUBLICATIONS

U.S. Appl. No. 15/944,480, Benayoud et al.
(Continued)

*Primary Examiner* — Taylor V Oh
(74) *Attorney, Agent, or Firm* — Clark & Elbing LLP

(57) ABSTRACT

The invention relates to methods and intermediates useful in the synthesis of eribulin.

18 Claims, 6 Drawing Sheets

(56) References Cited

U.S. PATENT DOCUMENTS

| | | | |
|---|---|---|---|
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,303,039 B2 | 4/2016 | Zhang et al. |
| 9,303,050 B2 | 4/2016 | Benayoud et al. |
| 9,382,262 B2 | 7/2016 | Endo et al. |
| 9,469,651 B2 | 10/2016 | Hu |
| 9,604,993 B2 | 3/2017 | Chase et al. |
| 9,695,188 B2 | 7/2017 | Hu et al. |
| 9,783,549 B2 | 10/2017 | Fang et al. |
| 9,802,953 B2 | 10/2017 | Chase et al. |
| 9,856,276 B2 | 1/2018 | Endo et al. |
| RE46,965 E | 7/2018 | Austad et al. |
| 10,030,032 B2 | 7/2018 | Hu et al. |
| 10,214,539 B2 | 2/2019 | Chase et al. |
| 10,221,189 B2 | 3/2019 | Fang et al. |
| 10,308,661 B2 | 6/2019 | Fang et al. |
| 10,450,324 B2 | 10/2019 | Hu et al. |
| 10,494,388 B2 | 12/2019 | Endo et al. |
| RE47,797 E | 1/2020 | Benayoud et al. |
| 2002/0103387 A1 | 8/2002 | Smith et al. |
| 2004/0092581 A1 | 5/2004 | Burzlaff et al. |
| 2006/0045846 A1 | 3/2006 | Horstmann et al. |
| 2007/0244187 A1 | 10/2007 | Austad et al. |
| 2009/0093649 A1 | 4/2009 | Nobis |
| 2009/0104285 A1 | 4/2009 | Littlefield et al. |
| 2009/0203771 A1 | 8/2009 | Inanaga et al. |
| 2010/0184860 A1 | 7/2010 | Yoshimura et al. |
| 2015/0065733 A1 | 3/2015 | Souza et al. |
| 2015/0158881 A1 | 6/2015 | Hu et al. |
| 2016/0152631 A1 | 6/2016 | Souza et al. |
| 2018/0002342 A1 | 1/2018 | Fang et al. |
| 2018/0037588 A1 | 2/2018 | Chase et al. |
| 2018/0118755 A1 | 5/2018 | Fang et al. |
| 2018/0162885 A1 | 6/2018 | Endo et al. |
| 2019/0010166 A1 | 1/2019 | Hu et al. |
| 2019/0144463 A1 | 5/2019 | Fang et al. |
| 2019/0161495 A1 | 5/2019 | Chase et al. |
| 2019/0263826 A1 | 8/2019 | Chase et al. |
| 2019/0308992 A1 | 10/2019 | Fang et al. |

FOREIGN PATENT DOCUMENTS

| | | |
|---|---|---|
| RU | 2489437 C2 | 8/2013 |
| SU | 652180 A1 | 3/1979 |
| WO | WO-93/17690 A1 | 9/1993 |
| WO | WO-98/09942 A1 | 3/1998 |
| WO | WO-99/65894 A1 | 12/1999 |
| WO | WO-2006/076100 A2 | 7/2006 |
| WO | WO-2008/010776 A1 | 1/2008 |
| WO | WO-2009/064029 A1 | 5/2009 |
| WO | WO-2012/147900 A1 | 11/2012 |
| WO | WO-2013/078559 A1 | 6/2013 |
| WO | WO-2013/142999 A1 | 10/2013 |
| WO | WO-2015/000070 A1 | 1/2015 |
| WO | WO-2015/066729 A1 | 5/2015 |
| WO | WO-2016/038624 A1 | 3/2016 |
| WO | WO-2018/006031 A1 | 1/2018 |
| WO | WO-2018/217894 A1 | 11/2018 |
| WO | WO-2019/136145 A1 | 7/2019 |

OTHER PUBLICATIONS

U.S. Appl. No. 16/031,629, Hu et al.
Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-4 (1992).
Aicher, Thomas Daniel, Thesis, Chapter 4, "Synthetic studies towards halichondrin B," Doctor of Philosophy in Chemistry, Harvard University, 35-54, 1989 (26 pages).
Alley et al. "Comparison of the relative efficacies and toxicities of Halichondrin B analogues," Proceedings of the AACR-NCI-EORTC Conference on Molecular Targets and Cancer Therapeutics. C230:257 (2005).
Ando et al., "Z-selective intramolecular Horner-Wadsworth-Emmons reaction for the synthesis of macrocyclic lactones," Org Lett. 12(7):1460-3 (2010).
Austad et al., "Commercial manufacture of Halaven®: chemoselective transformations en route to structurally complex macrocyclic ketones," Synlett. 24 (2013). Supporting Information, (13 pages.).
Austad et al., "Commercial manufacture of Halaven®: chemoselective transformations en route to structurally complex macrocyclic ketones," Synlett. 24(3):333-7 (2013).
Austad et al., "Process development of Halaven®: synthesis of the C14-C35 fragment via iterative Nozaki-Hiyama-Kishi reaction—Williamson ether cyclization," Synlett. 24(3):327-32 (2013).
Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).
Bernet et al., "Carbocyclische verbindungen aus monosacchariden. I. Umsetzungen in der glucosereihe," Helv Chim Acta. 62(6):1990-2016 (1979). (English abstract included).
Blanchette et al., "Horner-Wadsworth-Emmons reaction: use of lithium chloride and an amine for base-sensitive compounds," Tetrahedron Lett. 25(21):2183-6 (1984).
Burke et al., "Enantioselective synthesis of a Halichondrin B C(20) → C(36) precursor," Tetrahedron Lett. 36(39):7023-6 (1995).
Burke et al., "Synthesis of a C(22)—C(34) Halichondrin B precursor via ring opening—double ring closing metathesis," J Org Chem. 63:8626-7 (1998).
Burke et al., "Synthesis of a C(22) → C(34) Halichondrin precursor via a double dioxanone-to-dihydropyran rearrangement," Tetrahedron Lett. 32(32):3961-4 (1991).
Burke et al., "Synthetic studies toward complex polyether macrolides of marine origin," Spec Publ R Soc Chem. 198:(Anti-Infectives) 73-85 (1997).
Chase et al., "Process development of Halaven®: Synthesis of the C1-C13 fragment from D-(−)-Gulono-1,4-lactone," Synlett. 24(3):323-6 (2013).
Chen et al., "Ni(II)/Cr(II)-mediated coupling reaction: An asymmetric process," J Org Chem. 60(17):5386-7 (1995).
Choi et al., "Asymmetric Ni(II)/Cr(II)-mediated coupling reaction: catalytic process," Org Lett. 4(25):4435-8 (2002).
Choi et al., "Supporting information for asymmetric Ni(II)/Cr(II)-mediated coupling reaction: catalytic process," Org Lett. 4(25) (2002) (8 pages).
Choi et al., "Synthetic studies on the marine natural product Halichondrins," Pure Appl Chem. 75(1):1-17 (2003).
Cooper et al., "Total Synthesis of Halichondrin B from common sugars: an F-ring intermediate from D-glucose and efficient construction of the C1 to C21 segment," Tetrahedron Lett. 34(51):8193-6 (1993).
Cunningham et al., "The influence of pH on the kinetic constants of alpha-chymotrypsin-catalyzed esterolysis," J Biol Chem. 221(1):287-99 (1956).
Dabydeen et al. "Comparison of the activities of the truncated Halichondrin B analog NSC 707389 (E7389) with those of the parent compound and a proposed binding site on tubulin," Mol Pharmacol. 70(6):1866-75 (2006).
Del Valle et al., "Total synthesis of (+)-trienomycins a and F via C—C bond-forming hydrogenation and transfer hydrogenation," J Am Chem Soc. 135(30):10986-89 (2013).
Dong et al. "New syntheses of E7389 C14-C35 and halichondrin C14-C38 building blocks: reductive cyclization and oxy-michael cyclization approaches," J Am Chem Soc. 131(43):15642-6 (2009).

(56) References Cited

OTHER PUBLICATIONS

Duan et al., "Synthetic studies on halichondrins: a new practical synthesis of the C.1-C.12 segment," Tetrahedron Lett. 34(47):7541-4 (1993).
Fleming et al., "Nitrile anion cyclizations," Tetrahedron. 58(1):1-23 (2002).
Gesinski et al., "Symmetric macrocycles by a Prins dimerization and macrocyclization strategy," available in PMC Nov. 1, 2010, published in final edited form as: Org Lett. 11(22):5342-5 (2009) (13 pages).
Guo et al., "Toolbox approach to the search for effective ligands for catalytic asymmetric Cr-mediated coupling reactions," J Am Chem Soc. 131(42):15387-93 (2009).
Hirata et al., "Halichondrins—antitumor polyether macrolides from a marine sponge," Pure Appl Chem. 58(5):701-10 (1986).
Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).
Horita et al., "Research on anti-tumor active site of marine source natural product, Halichondrin B.," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16-C26 fragments via construction of the D ring by a highly stereocontrolled iodoetherification," Synlett. 40-43 (1994).
Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed Lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide isolated from a marine sponge. 9. Synthesis of the C16-C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals*. Fereidoon Shahidi and Chi-Tang Ho, 386-397 (2000).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al., "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kim et al., "New syntheses of E7389 C14-C35 and Halichondrin C14-C38 building blocks: double-inversion approach," J Am Chem Soc. 131(43):15636-41 (2009).
Kurosu et al., "Fe/Cr- and Co/Cr-mediated catalytic asymmetric 2-Haloallylations of aldehydes," J Am Chem Soc. 126(39):12248-9 (2004).
Kurosu et al., "Supporting information for Fe/Cr- and Co/Cr-mediated catalytic asymmetric 2-haloallylations of aldehydes," J Am Chem Soc. 126(39) (2004) (31 pages).
Mattocks, "371. Novel reactions of some alpha-acyloxy acid chlorides," J Chem Soc. Resumed. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Namba et al., "New catalytic cycle for couplings of aldehydes with organochromium reagents," Org Lett. 6(26):5031-3 (2004).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Nicolaou et al., "Total synthesis of brevetoxin A: Part 3: construction of GHIJ and BCDE ring systems," Chem Eur J. 5(2):628-45 (1999).
Nicolaou et al., "Total synthesis of the CP molecules CP-263,114 and CP-225,917—Part 1: synthesis of key intermediates and intelligence gathering," Angew Chem Int Ed. 38(11):1669-75 (1999).
Ritter, "Synthetic transformations of vinyl and aryl triflates," Synthesis: Reviews. 8:735-62 (1993).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Seletsky et al. "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48):8647-50 (1996).
Stamos et al., "New synthetic route to the C.14-C.38 segment of Halichondrins," J Org Chem. 62(22):7552-3 (1997).
Stamos et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Stamos et al., "Synthetic studies on Halichondrins: a practical synthesis of the C.1-C.13 segment," Tetrahedron Lett. 37(48):8643-6 (1996).
Sutherland et al., "The synthesis of 6alpha- and 6beta-fluoroshikimic acids," J Chem Soc Chem Commun. 18:1386-7 (1989).
Takai et al., "Reactions of alkenylchromium reagents prepared from alkenyl trifluoromethanesulfonates (triflates) with chromium(II) chloride under nickel catalysis" J Am Chem Soc. 108(19):6048-50 (1986).
Tokunaga et al., "Asymmetric catalysis with water: efficient kinetic resolution of terminal epoxides by means of catalytic hydrolysis," Science. 277(5328):936-8 (1997).
Towle et al. "Halichondrin B macrocyclic ketone analog E7389: medicinal chemistry repair of lactone ester instability generated during structural simplification to clinical Candidate" Annual Meeting of the American Association for Cancer Research, Apr. 6-10, 2002, 5721 (3 pages).
Towle et al. "In vitro and in vivo anticancer activities of synthetic macrocyclic ketone analogues of Halichondrin B," Cancer Res. 61(3):1013-21 (2001).
Uemura et al., "Norhalichondrin A: an antitumor polyether macrolide from a marine sponge," J Am Chem Soc. 107(16):4796-8 (1985).
Vandat et al., "Phase II study of eribulin mesylate, a Halichondrin B analog, in patients with metastatic breast cancer previously treated with an anthracycline and a taxane," J Clin Oncol. 27(18):2954-61 (2009).
Varseev et al, "Enantioselective total synthesis of (+)-neosymbioimine," Org Lett. 9(8):1461-4 (2007).
Wan et al., "Asymmetric Ni(II)/Cr(II)-mediated coupling reaction: Stoichiometric process," Org Lett. 4(25):4431-4 (2002) Supporting Information, 8 pages.
Wang et al., "Facile preparation of peracetates and per-3-bromobenzoates of alpha-mono- and disaccharides," Molecules. 10(10):1325-34 (2005).
Wang et al., "Structure-activity relationships of halichondrin B analogues: modifications at C.30-C.38" Bioorg Med Chem Lett. 10(10):1029-32 (2000).
Xie et al., "Synthesis of the C20-C26 building block of Halichondrins via a regiospecific and stereoselective SN2' reaction," Org Lett. 4(25): 4427-9 (2002).

(56) References Cited

OTHER PUBLICATIONS

Yamamoto et al., "Total synthesis of halichondrin C," J Am Chem Soc. 134(2):893-6 (2012).
Yang et al., "Second generation synthesis of C27-C35 building block of E7389, a synthetic Halichondrin analogue," Org Lett. 11(20): 4516-9 (2009).
Youssefyeh, "Acylations of ketals and enol ethers," J Am Chem Soc. 85(23):3901-2 (1963).
Yu et al., "From micrograms to grams: scale-up synthesis of eribulin mesylate," Nat Prod Rep. 30(9):1158-64 (2013).
Yu et al., "Macrocyclic drugs and synthetic methodologies toward macrocycles," Molecules 18(6):6230-68 (2013).
Yu et al., "New synthetic route to the C.14-C.21 fragment of Halichondrin B," Book of Abstracts. 219th ACS National Meeting, San Francisco, CA, Mar. 26-30, (2000) (1 page).
Yu et al., Discovery of E7389 a fully synthetic macrocyclic ketone analog of Halichondrin B. *Anticancer Agents from Natural Product.* CRC Press, 241-265 (2005).
Zheng et al., "Macrocyclic ketone analogues of halichondrin B," Bioorg Med Chem Lett. 14(22): 5551-4 (2004).
Zheng et al., "Synthetic macrocyclic ketone analogs of halichondrin B: structure-activity relationships" Proceedings of the American Association for Cancer Research, 41:301, Abstract #1915 (2000).
U.S. Appl. No. 16/284,405, Chase et al.
U.S. Appl. No. 16/387,820, Fang et al.
Extended European Search Report for European Application No. 17750887.6, dated Jul. 11, 2019 (6 pages).
Kong et al., "Total synthesis of the spirocyclic imine marine toxin (−)-gymnodimine and an unnatural C4-epimer," J Am Chem Soc. 133(49): 19844-56 (2011).
Namba et al., "A simple but remarkably effective device for forming the C8-C14 polycyclic ring system of halichondrin B," J Am Chem Soc. 126(25): 7770-1 (2004) (10 pages).
Narayan et al., "Novel second generation analogs of eribulin. Part II: Orally available and active against resistant tumors in vivo," Bioorg Med Chem Lett. 21(6):1634-8 (2011).
PubChem Compound Summary for CID 10501910, <https://pubchem.ncbi.nlm.nih.gov/compound/10501910>, created Oct. 25, 2006, retrieved Aug. 30, 2017 (8 pages).
International Search Report and Written Opinion dated Apr. 13, 2017 for International Application No. PCT/US2017/017501, Baran et al., "Intermediates in the Synthesis of Eribulin and Related Methods of Synthesis," filed Feb. 10, 2017 (13 pages).
Yu et al., "Atom-based enumeration: new eribulin analogues with low susceptibility to P-glycoprotein-mediated drug efflux," Bioorg Med Chem Lett. 22(24):7363-6 (2012).
U.S. Appl. No. 16/684,332, Benayoud et al.
Gradillas et al., "Macrocyclization by ring-closing metathesis in the total synthesis of natural products: reaction conditions and limitations," Angew Chem Int Ed Engl. 45(37): 6086-6101 (2006).
Ward et al., "Catalytic enantioselective diels-alder reaction by self-assembly of the components on a Lewis acid template," Org Lett. 7(16):3533-6 (2005) (Abstract only) (2 pages).

INTERMEDIATES IN THE SYNTHESIS OF ERIBULIN AND RELATED METHODS OF SYNTHESIS

BACKGROUND OF THE INVENTION

Halichondrin B is a structurally complex, macrocyclic compound that was originally isolated from the marine sponge *Halichondria okadai*, and subsequently was found in *Axinella* sp., *Phakellia carteri*, and *Lissodendoryx* sp. Eribulin is a synthetic analog of halichondrin B. The mesylate salt of eribulin (eribulin mesylate, which is marketed under the trade name HALAVEN®) is approved for the treatment of patients with breast cancer who have previously received at least two chemotherapeutic regimens for the treatment of metastatic disease that included an anthracycline and a taxane in either the adjuvant or metastatic setting.

SUMMARY OF THE INVENTION

The invention provides eribulin and diastereomers thereof containing carbon-11, as well as methods of synthesizing eribulin by a two-step process including a nitro aldol reaction and a reduction.

In a first aspect, the invention provides a compound according to formula (I),

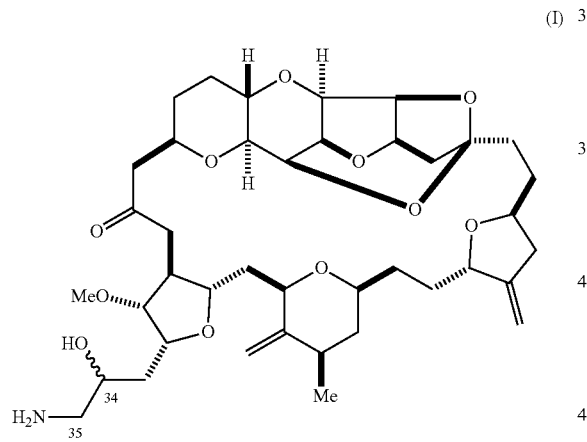

(I)

or a pharmaceutically acceptable salt thereof, wherein the compound contains carbon-11.

In some embodiments, the stereochemical configuration at position 34 of the compound is (S). In some embodiments, the stereochemical configuration at position 34 of the compound is (R). In some embodiments, the carbon-11 is located at position 35 of the compound of formula (I).

In some embodiments, the compound is the mesylate salt of formula (I).

The compound of formula (I) may also be in the form of an isotopically enriched composition, i.e., in carbon 11. The term "isotopically enriched," as used herein, refers to a composition including an isotope, e.g., $^{11}C$, at a position in the compound in an abundance greater than other isotopes, e.g., $^{12}C$, at that same position. Typically and depending on the isotope, compositions enriched in a particular isotope may have an isotopic enrichment factor of at least 5, at least 10, at least 50, at least 500, at least 2000, at least 3000, at least 6000, or at least 6600, e.g., relative to $^{12}C$.

In an additional aspect, the invention relates to a method of synthesizing a compound according to formula (I), by reacting an aldehyde according to formula (II):

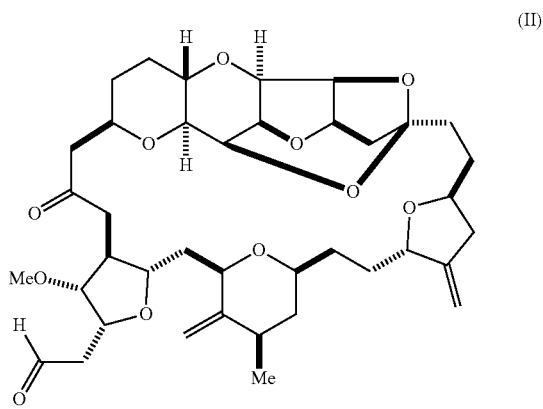

(II)

with nitromethane, e.g., containing carbon-11, under Henry reaction conditions to form a compound according to formula (III):

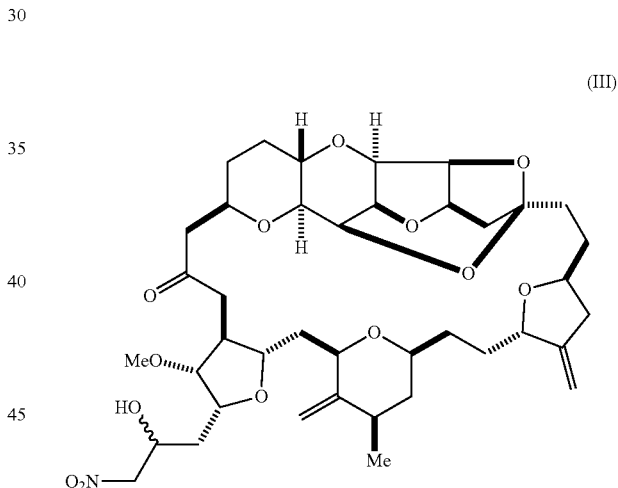

(III)

1p;2pand reducing the compound according to formula (III) with a reducing agent to form the compound according to formula (I).

In some embodiments, the method includes dissolving the aldehyde in an alcohol, e.g., methanol, to form a solution. In some embodiments, the solution has a concentration of from 0.01 M to 0.5 M, e.g., about 0.1 M. In some embodiments, the method includes adding from 1 to 10,000 molar equivalents of the nitromethane to the aldehyde, e.g., about 1000 molar equivalents of the nitromethane to the aldehyde.

In some embodiments, the method includes adding a base, e.g., sodium hydroxide, to a mixture containing the aldehyde and the nitromethane.

In some embodiments, the compound according to formula (III) is reduced by a lanthanide salt, such as samarium (II) iodide. In some embodiments, the method includes dissolving the compound according to formula (III) in an alcohol, e.g., methanol, to form a solution. In some embodiments, the solution has a concentration of compound according to formula (III) from 0.01 mM to 1 mM, e.g., about 0.7 mM. In some embodiments, the reducing agent is present in a solution at a concentration of from 0.01 M to 1 M, e.g., about 0.1 M. In some embodiments, the method includes mixing from 2 molar equivalents to 1000 molar equivalents of the reducing agent with the compound according to formula (III).

In another aspect, the invention provides a method of synthesizing a compound according to formula (I), by reacting an aldehyde according to formula (II):

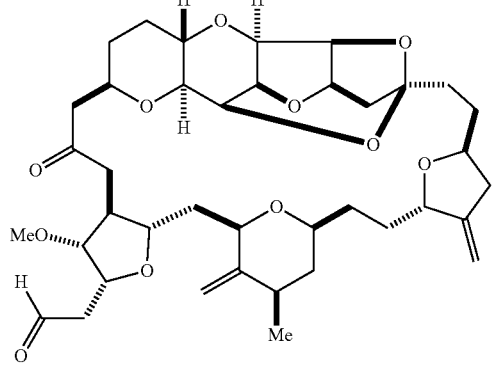

(II)

with a cyanide salt, e.g., potassium cyanide, under conditions to form a cyanohydrin according to formula (IV):

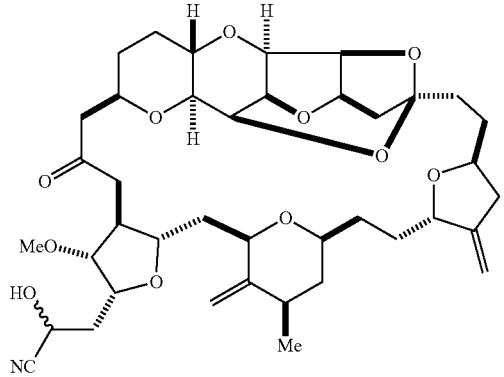

(IV)

and reducing the cyanohydrin according to formula (IV) with a reducing agent to form the compound according to formula (I). In some embodiments, the reducing agent is a silane, such as triethylsilane, used, for example, in combination with a Lewis acid, such as tris(perfluorophenyl) borane. In some embodiments, the cyanide salt contains carbon-11 (e.g., K$^{11}$CN).

In some embodiments, the aldehyde is synthesized by reacting a diol according to formula (V):

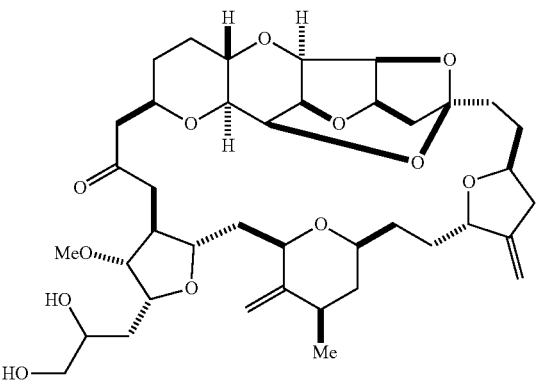

(V)

with an oxidizing agent, e.g., sodium periodate.

In some embodiments, any of the methods may further include salifying the compound of formula (I) to produce a pharmaceutically acceptable salt thereof, e.g., the mesylate salt. The methods may also include separating the diastereomers of the compound of formula (I) to isolate eribulin, or a pharmaceutically acceptable salt thereof, e.g., the mesylate salt.

In another aspect, the invention features a compound according to formula (II):

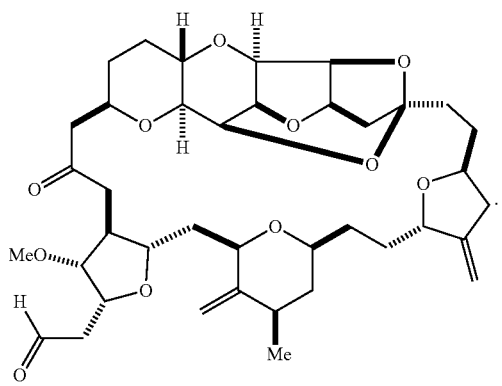

(II)

In another aspect, the invention features a compound according to formula (IV):

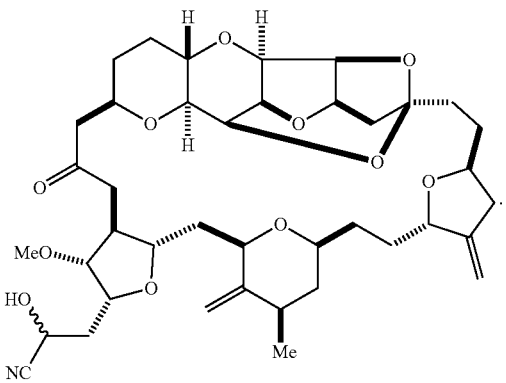

(IV)

The invention further provides a pharmaceutical composition comprising an effective amount of a carbon-11 containing compound of formula (I) or an isotopically enriched composition of a compound of formula (I) and a pharmaceutically acceptable carrier.

In an additional aspect, the invention provides a method of using a carbon-11 containing compound of formula (I) to image a subject, e.g., a human subject. In some embodiments, the method includes administering the compound to the subject and detecting the presence of the compound. In some embodiments, the detecting includes analyzing the subject by positron emission tomography.

DETAILED DESCRIPTION

Figure 1:
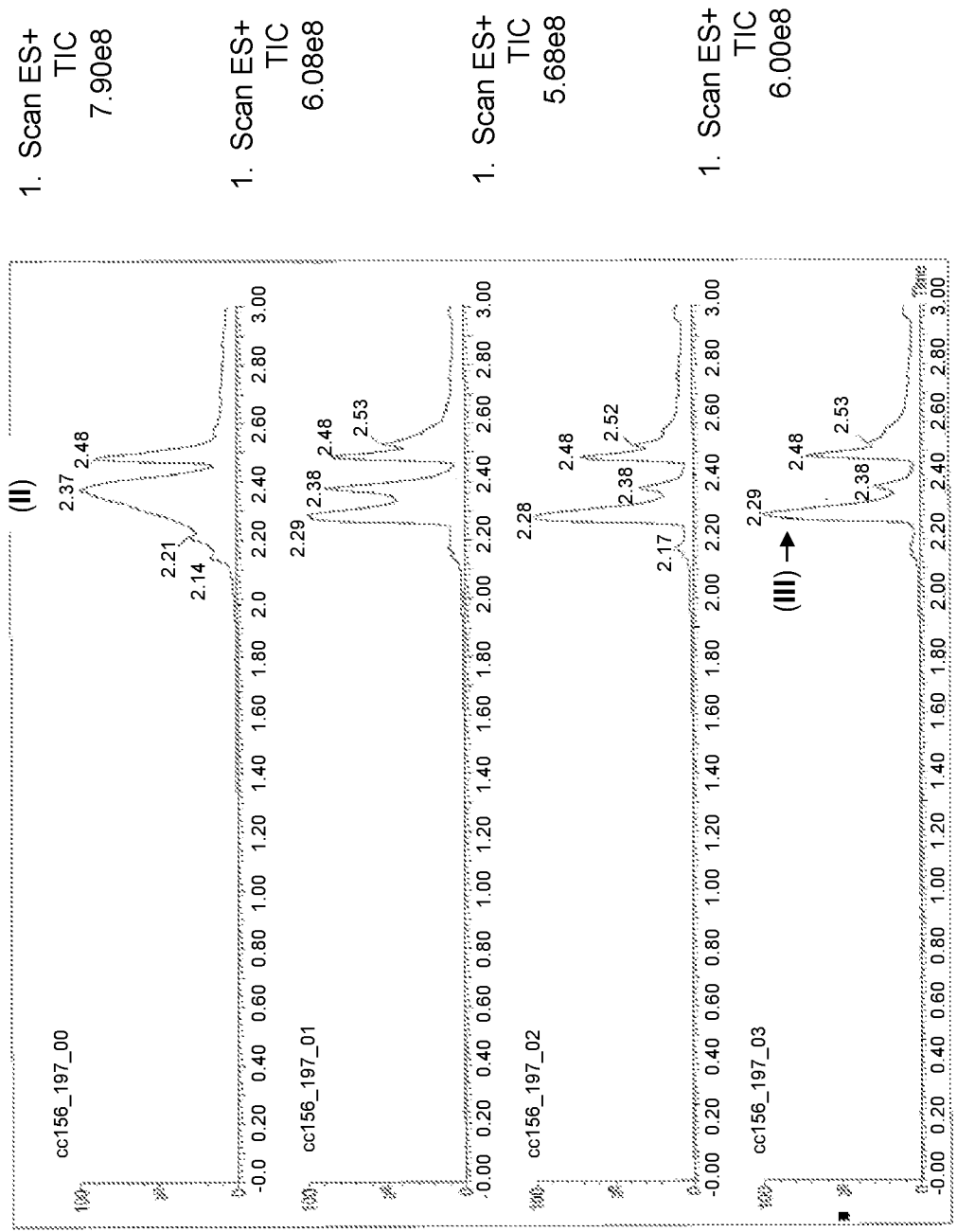
FIG. 1 shows a series of chromatograms tracing the conversion of compound (II) to compound (III) as described in Example 1. From top to bottom, the chromatograms correspond to the reaction mixture sampled at about 5 minutes, about 30 minutes, about 1 hour and 50 minutes, and about 3 hours from the beginning of the addition of nitromethane and sodium hydroxide to compound (II) as outlined in Example 1.

The invention provides eribulin and diastereomers thereof, represented by formula (I), below, that contain carbon-11, as well as related methods of synthesis.

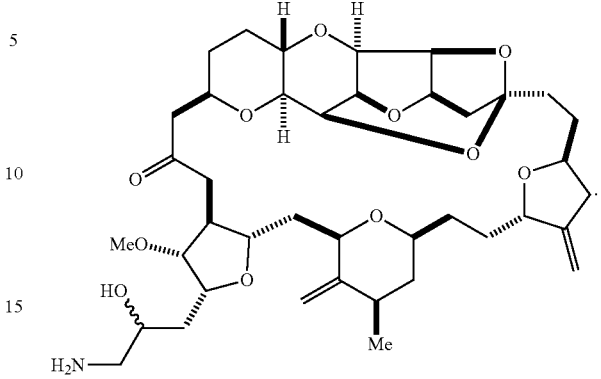

(I)

The invention further features a pharmaceutically acceptable salt of the compound of formula (I), e.g., the mesylate salt.

The compounds produced by the methods of the invention, such as eribulin or diastereomer thereof containing carbon-11 at position 35 of the molecule, can be used for a variety of purposes. Eribulin is a known chemotherapeutic agent, and eribulin synthesized by the methods of the invention can be administered to a human patient suffering from cancer, optionally in combination with additional chemotherapeutic agents, in order to treat the cancer. Additionally, as carbon-11 is a well-established radiolabel for positron emission tomography, eribulin containing carbon-11 can be administered to a patient in order to visualize a sample within a subject, such as a particular organ or tissue within the subject. For instance, eribulin containing carbon-11 may be administered to a patient in order to image one or more solid tumors within a subject, e.g., that is undergoing chemotherapeutic treatment.

Using the methods of the invention, eribulin can be synthesized under Henry reaction conditions, e.g., as follows:

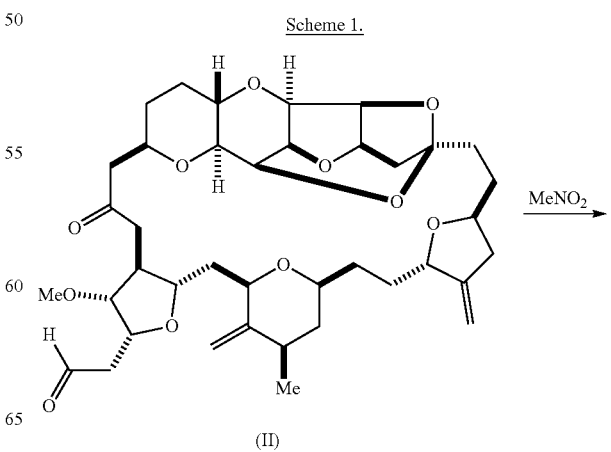

Scheme 1.

(II)

-continued

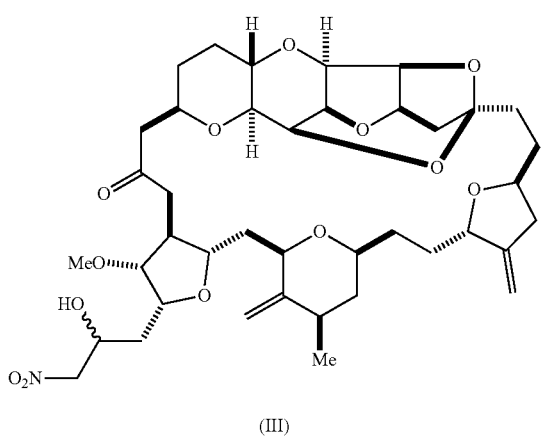

(III)

According to the methods of the invention, compound (III) can be reduced, e.g., using lanthanide salt, such as samarium (II) iodide. Other suitable reducing agents are known in the art. For instance, compound (III) can be reduced according to the following reaction scheme:

Scheme 2.

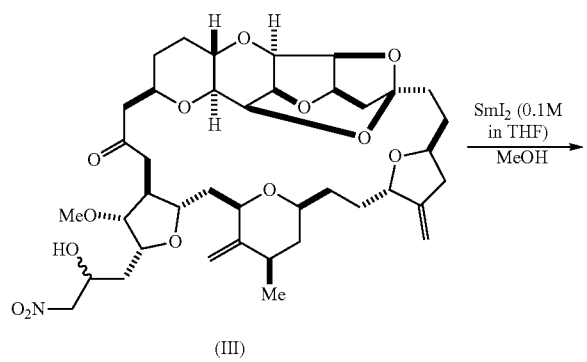

Optionally, eribulin can be synthesized using a one- or two-pot procedure, e.g., as described in Scheme 3, below. In this process, compound (II) is transformed to compound (III) by a nitro aldol process using nitromethane. A reducing agent, such as SmI$_2$, can then be mixed directly with the reaction mixture containing compound (III). As shown in Scheme 3, below, and as described in further detail in the Examples, this process can be performed either by adding the reducing agent directly to the reaction mixture following the Henry reaction, or by transferring the reaction mixture containing compound (III) to a vessel containing the reducing agent. Acidic workup may also be performed with pivalic acid instead of acetic acid.

Scheme 3.

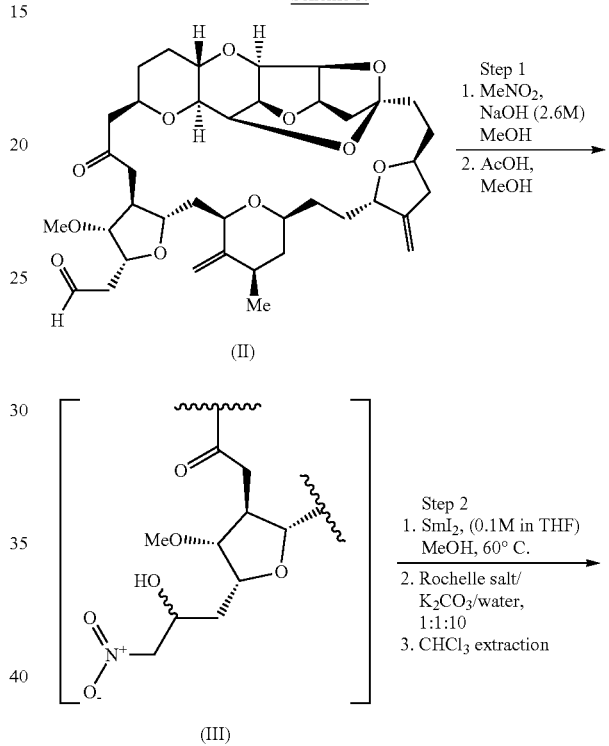

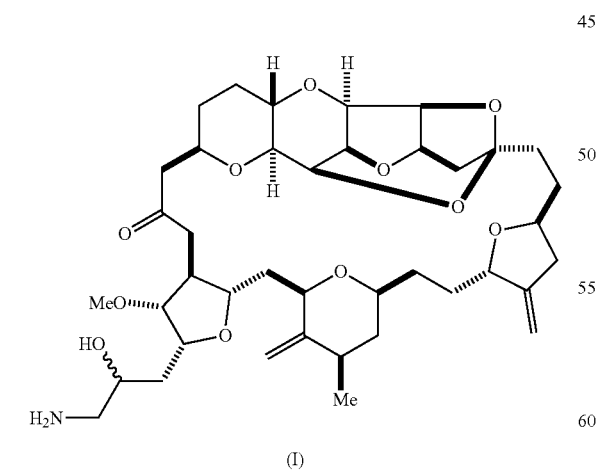

Using the methods of the invention, compound (II) can be synthesized by the oxidation of a diol according to formula (V). For instance, compound (II) can be prepared by sodium periodate-mediated oxidation of diol (V), as illustrated in reaction scheme 4, below.

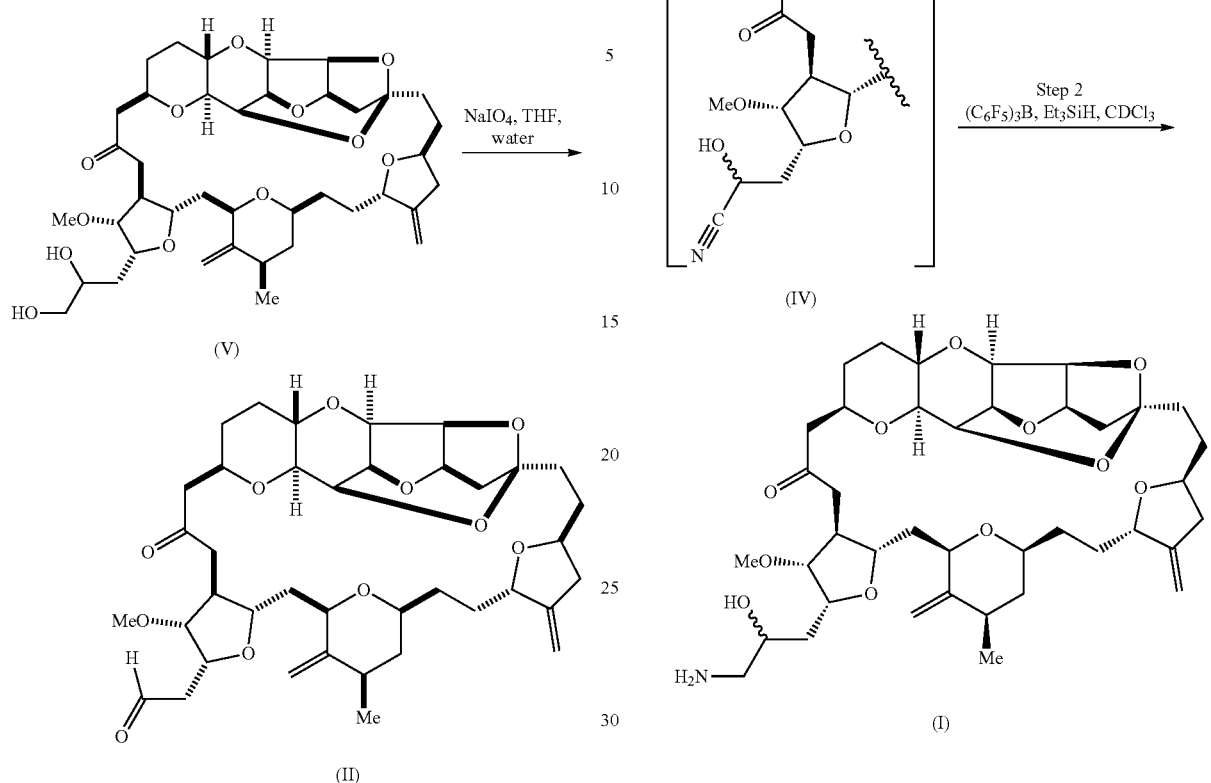

Using the methods of the invention, eribulin alternatively be synthesized by reacting aldehyde (II) with a cyanide salt, such as potassium cyanide, in order to form a cyanohydrin represented by formula (IV), below. The cyanohydrin thus obtained can subsequently be reduced to generate eribulin. This two-step process is depicted in Scheme 5, below. The nitrile substituent of cyanohydrin (IV) can be reduced to an amine, e.g., by reaction of the cyanohydrin with a reducing agent, such as a silane, e.g., diethylsilane or triethylsilane, in the presence of a Lewis acid, such as tris(perfluorophenyl)borane (Chang et al. J. Org. Chem. 2015, 80, 7281-7287).

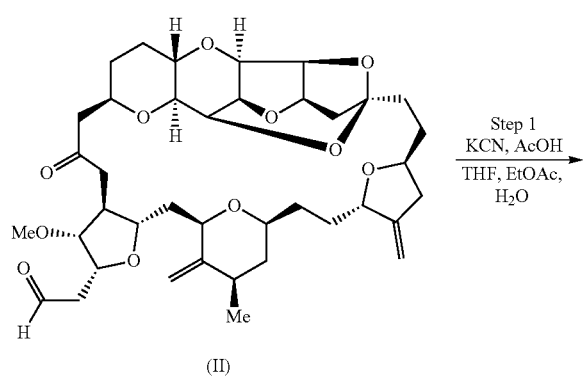

Eribulin can be separated from its C-34 diastereomer using standard techniques, such as HPLC.

Salification reaction conditions are known in the art. Salification of eribulin can afford a pharmaceutically acceptable salt of eribulin (e.g., eribulin mesylate). In particular, the salification reaction can involve contacting eribulin with a Brønsted acid (e.g., a pharmaceutically acceptable Brønsted acid (e.g., methanesulfonic acid)) to afford a pharmaceutically acceptable salt of eribulin (e.g., *Handbook of Pharmaceutical Salts: Properties, Selection and Use*, ed.: Stahl and Wermuth, Wiley-VCH/VHCA, Weinheim/Zurich, 2002). Pharmaceutically acceptable salts of eribulin, e.g., eribulin mesylate, can be formed by methods known in the art, e.g., in situ during the final isolation and purification of the compound or separately by reacting the free base group with a suitable organic acid. In one example, eribulin is treated with a solution of MsOH and $NH_4OH$ in water and acetonitrile. The mixture is concentrated. The residue is dissolved in DCM-pentane, and the solution is added to anhydrous pentane. The resulting precipitate is filtered and dried under high vacuum to provide eribulin mesylate.

Formulations

Compounds or isotopically enriched compositions of the invention can be formulated as pharmaceutically acceptable salts, which are a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. A preferred salt is the mesylate salt.

Compounds or isotopically enriched compositions of the invention can also be formulated as pharmaceutical compositions, e.g., by combining an effective amount of the compound or isotopically enriched composition with a pharmaceutically acceptable carrier. An effective amount is typically the amount needed to image a subject by positron emission topography.

Pharmaceutical compositions can be prepared using standard methods known in the art, or can be obtained from commercial sources. A compound of formula (I), e.g., eribulin, is typically provided in liquid form, for intravenous administration.

Pharmaceutical compositions used in the invention can be prepared by, for example, mixing or dissolving the active ingredient(s), having the desired degree of purity, in a physiologically acceptable carrier (see, e.g., Remington's Pharmaceutical Sciences (20th edition), ed. A. Gennaro, 2000, Lippincott, Williams & Wilkins, Philadelphia, Pa.). Acceptable carriers include water and saline, optionally including buffers such as phosphate, citrate, or other organic acids; antioxidants including butylated hydroxytoluene (BHT), butylated hydroxyanisole (BHA), ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, or other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, the formulations of the invention contain a pharmaceutically acceptable preservative. In some embodiments the preservative concentration ranges from 0.1 to 2.0%, typically v/v. Suitable preservatives include those known in the pharmaceutical arts, such as benzyl alcohol, phenol, m-cresol, methylparaben, and propylparaben. Further, the formulations of a compound of formula (I), e.g., eribulin, can optionally include a pharmaceutically acceptable salt, such as sodium chloride at, for example, about physiological concentrations. Thus, in one example, the compound of formula (I), e.g., eribulin (e.g., eribulin mesylate), is formulated in 0.9% Sodium Chloride Injection (USP).

The formulations noted above (and others) can be used for parenteral administration of the drugs. Thus, the drugs can be administered by routes including intravenous, intra-tumoral, peri-tumoral, intra-arterial, intra-dermal, intra-vesical, ophthalmic, intramuscular, intradermal, intraperitoneal, pulmonary, subcutaneous, and transcutaneous routes. Other routes can also be used including, for example, transmucosal, transdermal, inhalation, intravaginal, rectal, and oral administration routes.

The dosage of compound of formula (I), e.g., eribulin, administered can differ markedly depending on the type of target disease, the choice of delivery method, as well as the age, sex, and weight of the patient, the severity of the symptoms, along with other factors.

EXAMPLES

The following methods illustrate the synthesis of compounds of formula (I) using reagents with the natural abundance of carbon isotopes. These processes may be modified by use of $^{11}$C-labeled nitromethane or $^{11}$C-labeled cyanide to produce $^{11}$C labeled compounds of formula (I).

Example 1. Synthesis of Compound of Formula (III) by Nitro Aldol Reaction

The aldehyde of formula (II) (278 mg, 0.398 mmol) was dissolved in methanol (2.780 mL), and nitromethane (21.45 μL, 1 eq., 0.398 mmol) and sodium hydroxide (2.6 M, 161 μL, 1.05 eq., 0.418 mmol) were subsequently added to the aldehyde solution. The ensuing reaction was allowed to proceed for about 3 hours, and the reaction mixture was periodically monitored by liquid chromatography/mass spectrometry (LC/MS). After 5 minutes, the ratio of product, compound of formula (III), to starting material was approximately 2:1. After about 30 minutes, only 5-10% of the aldehyde remained, as the reaction mixture contained predominantly the nitro-containing compound or formula (III). After about 1 hour and 50 minutes, no change in reaction mixture composition was observed relative to the reaction mixture analyzed after 30 minutes. Additionally, after about 3 hours, no change in reaction mixture composition was observed relative to the reaction mixture analyzed after 30 minutes (FIG. 1).

The reaction was subsequently quenched by adding acetic acid (23.91 μL, 0.418 mmol) followed by the drop-wise addition of water (7 mL) to obtain a white suspension. The suspension was filtered and dried under a stream of $N_2$ to yield 235 mg of compound of formula (III) as a white powder (0.31 mmol, 78%).

Example 2. Reduction of Compound of Formula (III) by Standard Addition Process

Figure 2:
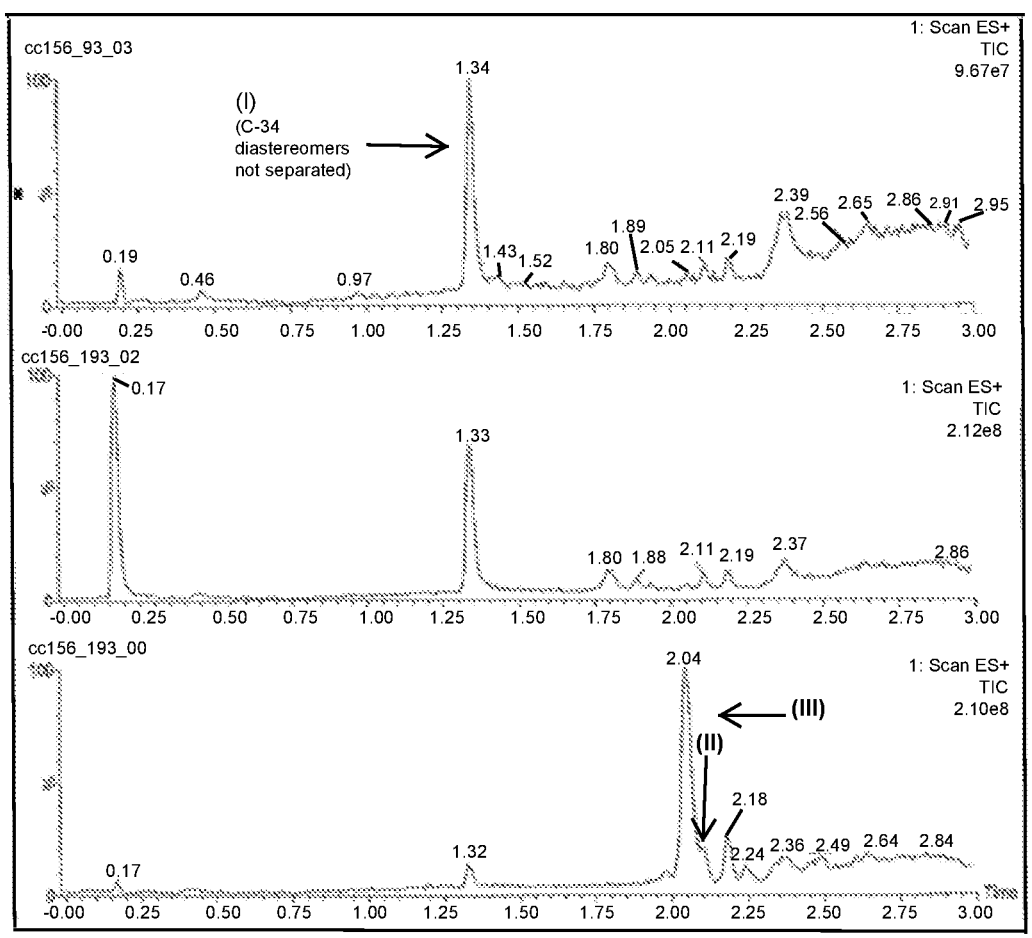
FIG. 2 shows a series of chromatograms tracing the conversion of compound (III) to compound (I) as described in Example 2. From bottom to top, the chromatograms correspond to the reaction mixture sampled at the start of the reaction, about 17 minutes following the addition of $SmI_2$ to the nitro adduct (III), and following the addition of Rochelle salt solution to the reaction mixture.

Compound of formula (III) (6.40 mg, 8.422 μmol) was dissolved in methanol (1.28 mL) and was degassed by $N_2$ sparge for 2 minutes. The solution was then gradually warmed to 55-60° C. A solution of $SmI_2$ (0.1 M in THF, 0.84 mL, 10 eq.) was then added to the solution of compound of formula (III) over the course of 2 minutes. The temperature of the reaction mixture at the beginning of the addition was 40° C. and was steadily increased to 50° C. during the addition. After 8 minutes from the beginning of the addition of the $SmI_2$ solution to compound of formula (III), the reaction was observed to be complete. No change in reaction composition was observed after 10 additional minutes. A solution containing Rochelle salt (potassium sodium tartrate), $K_2CO_3$, and water (1:1:10 by mole, 1 mL) was subsequently added to the reaction mixture, and the resulting suspension was stirred for 2 minutes. Chloroform (1 mL) was then added, and the reaction was stirred for an additional 2 minutes (FIG. 2). The bottom layer was removed, and the aqueous layer was extracted twice with chloroform. Thin layer chromatography (TLC) analysis of the extracts revealed that compound (I) was contained within the first two chloroform solutions. The extracts were combined and concentrated to yield 9 mg crude product as a pale yellow solid.

Figure 3A:
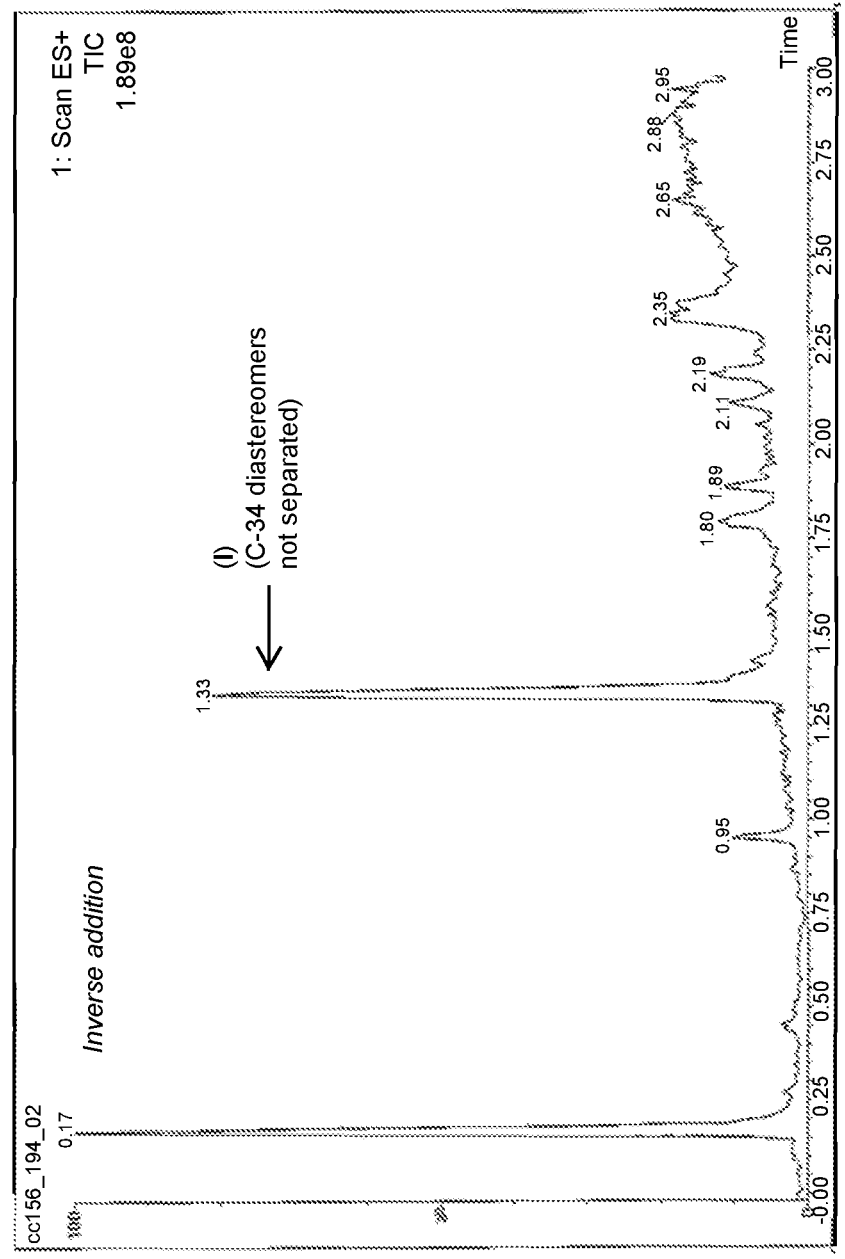
FIG. 3A is a chromatogram obtained from analysis of the reaction mixture following the inverse addition of nitro adduct to reducing agent as described in Example 3.
Figure 3B:
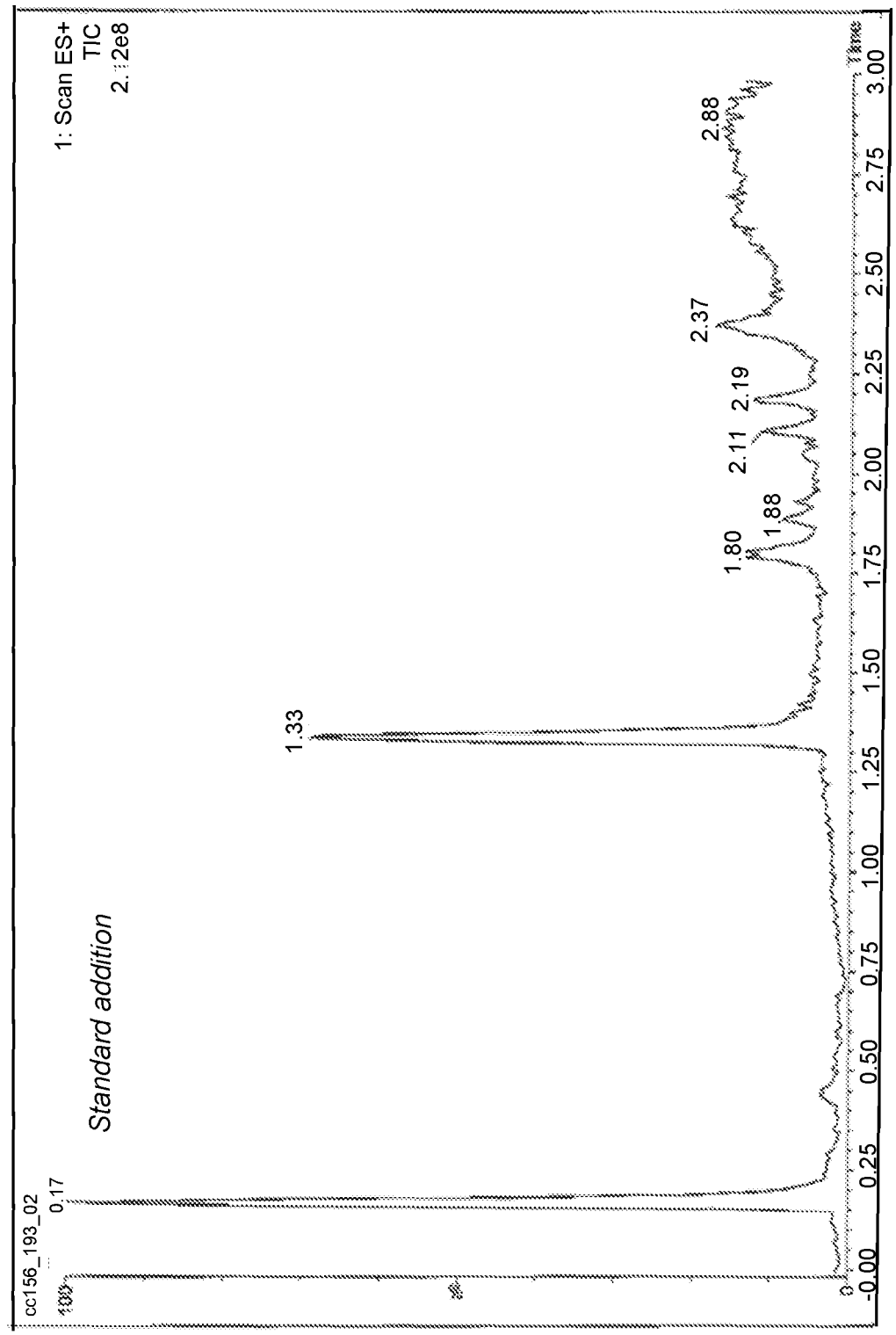
FIG. 3B is a chromatogram obtained from analysis of the reaction mixture following the addition of reducing agent to nitro adduct as described in Example 2.

Example 3. Reduction of Compound of Formula (III) by Inverse Addition Process Compound of formula (III) (6.40 mg, 8.422 μmol) was dissolved in methanol (1.28 mL) and was degassed by $N_2$ sparge for 2 minutes. In a separate flask, a solution of $SmI_2$ was prepared (0.1 M in THF, 0.84 mL, 10 eq.) and was gradually warmed to 55-60° C. The solution of compound of formula (III) was then added to the solution of $SmI_2$ over the course of 3 minutes. The temperature of the reaction mixture at the beginning of the addition was 64° C. and was 60° C. at the end of the addition. The reaction mixture after 12 minutes from the beginning of the addition of the $SmI_2$ solution to compound of formula (III) was monitored by LC/MS, and the results were compared to the LC/MS trace obtained following the standard addition process described in Example 2. This comparison is shown in FIGS. 3A and 3B.

After 12 minutes from the beginning of the addition of the $SmI_2$ solution to compound of formula (III), the mixture was cooled to room temperature. A solution containing Rochelle salt, $K_2CO_3$, and water (1:1:10 by mole, 1 mL) was subsequently added to the reaction mixture, and the resulting suspension was stirred for 2 minutes. Chloroform (1 mL) was then added, and the reaction was stirred for an additional 2 minutes. The bottom layer was removed, and the aqueous layer was extracted twice with chloroform. Thin layer chromatography (TLC) analysis of the extracts revealed that compound of formula (I) was contained within the first two chloroform solutions. The extracts were combined and concentrated to yield 16 mg crude product as a pale yellow solid.

Example 4. One-Pot Procedure for Synthesis of Compound of Formula (I) by a Tandem Nitro Aldol/Reduction Process Step 1: A stock solution of carbon-11-labelled nitromethane (3.5 μL) was added to methanol (1.5 mL) sparged with $N_2$. Compound of formula (II) (15.00 mg, 0.02 mmol) was dissolved in the nitromethane/methanol solution (0.15 mL solution, 0.262 mg nitromethane, 4.293 μmol, 0.2 eq.) in a $N_2$ purged, 1.5-mL vial equipped with stir bar and silicon polytetrafluoroethylene (PTFE) septum. A 5-10 μL-aliquot of the resulting mixture was removed and diluted in 0.25 mL methanol for analysis. A sodium hydroxide solution (2.6 M, 1.65 μL, 4.29 μmol) was then added to the mixture, and the ensuing reaction was allowed to proceed for 16 minutes. Acetic acid (12.28 μL, 0.215 mmol, 10 eq.) was then added to the reaction mixture, which was then diluted with $N_2$-sparged methanol (3 mL).

Figure 4:
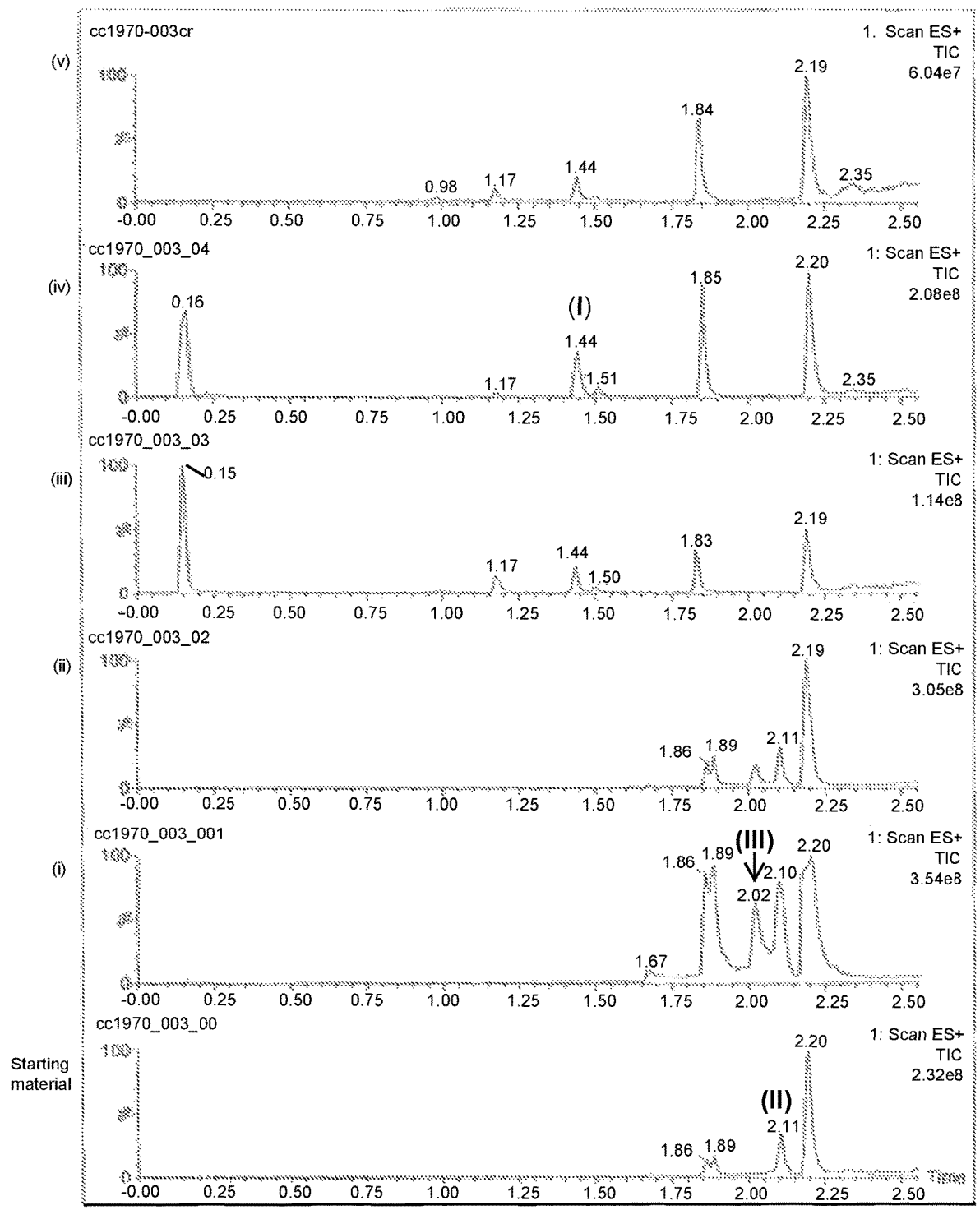
FIG. 4 shows a series of chromatograms tracing the conversion of compound (II) to compound (I) as described in Example 4. From bottom to top, the chromatograms correspond to starting material, (i) reaction mixture following the addition of nitromethane and sodium hydroxide, (ii) reaction mixture following quenching in acetic acid, (iii) and (iv) reaction mixture following addition of $SmI_2$, and (v) reaction mixture after work up.

Step 2: A solution of $SmI_2$ (0.1 M in THF, 2.15 mL, 0.215 mmol) was added to a $N_2$-purged, 7-mL conical microwave vial equipped with silicon PTFE crimp cap and stir bar. The mixture was warmed to 60° C. The nitro adduct formed in step 1 was then added to the $SmI_2$ solution slowly over the course of 2 minutes. The temperature of the ensuing mixture at the beginning of the addition process was 38° C., and the temperature of the mixture at the end of the addition process was 45° C. and rising. After 12 minutes from the start of the addition process, the reduction was observed to be complete. The reaction mixture was then gradually cooled to room temperature, and the methanol was evaporated by $N_2$ stream. A solution containing Rochelle salt, $K_2CO_3$, and water (1:1:10 by mole, 3 mL) was then added to the reaction mixture. After 5 minutes, chloroform (2 mL) was added to the mixture, which was then vigorously stirred. The layers were allowed to partition, and the bottom layer (chloroform) was removed. The chloroform extraction was repeated a second time, and the extracts were analyzed by TLC. It was observed that the product (compound of formula (I)) was predominantly in the first extract, with trace quantities of product observed in the second extract. The aqueous layer was found to contain no product. LC/MS traces recorded during various stages of Step 1 and Step 2 are shown in FIG. 4.

Example 5. Synthesis of Compound of Formula (II) by Oxidation of a Diol Precursor The diol of formula (V) (126 mg, 0.172 mmol) was dissolved in THF (1.6 mL) and water (0.88 mL). Sodium periodate (55.3 mg, 0.259 mmol) was added to form a mixture, which was subsequently stirred at room temperature. The progress of the ensuing oxidation reaction was monitored by LCMS analysis. A white precipitate formed within 10 minutes of mixing. After 2 hours, water (15 mL) was added, and the mixture was extracted with ethyl acetate (3×15 mL). Ethanol 1 (mL) was added to the mixture causing layers to partition. The combined extracts were subsequently washed with water and then concentrated to provide the aldehyde of formula (II) as white solid (115 mg, 0.9 wt, 95% yield).

Example 6. Purification of Eribulin by Reverse-Phase High Pressure Liquid Chromatography (RP-HPLC)

Following the one-pot procedure described in Example 4, compound of formula (I) was purified by RP-HPLC using a two-component mobile phase and gradient elution profile as described in Tables 1 and 2, below. C18 columns were obtained from ACE® (Aberdeen, Scotland). Solvent A: 760 mL water and 240 mL acetonitrile mixed together, 7.0±0.2 g ammonium trifluoromethanesulfonate, 3.0 mL of 1.0 M tetrabutylammonium dihydrogenphosphate aqueous solution added, and pH adjusted to between 6.9 and 7.1 with either 5.6% ammonium hydroxide solution or 1 M HCl. Solvent B: 300 mL of water, 7000 mL of acetonitrile, and 20 mL of 2-propanol mixed together, 7.0±0.2 g ammonium trifluoromethanesulfonate, 3.0 mL of 1.0 M tetrabutylammonium dihydrogenphosphate aqueous solution added, and pH adjusted to between 6.9 and 7.1 with either 5.6% ammonium hydroxide solution or 1 M HCl.

TABLE 1

Summary of parameters used for HPLC analysis

| | |
|---|---|
| HPLC column | 3.0 mm × 15 cm column containing 3 μm packing (L1/USP) (e.g., ACE ® C18, 3 μm particle size) |
| Column temperature | Constant temperature of approximately 40° C. |
| Gradient profile | Linear gradient (see below) |
| Injection | 5 μL |
| Detection (UV) | UV absorbance at 200 nm |
| Run time | 90 minutes |

TABLE 2

| HPLC gradient profile | | | |
|---|---|---|---|
| Time (min) | % Solvent A | % Solvent B | Flow rate (mL/min) |
| 0 | 100 | 0 | 0.50 |
| 55 | 100 | 0 | 0.50 |
| 75 | 0 | 100 | 0.63 |
| 85 | 0 | 100 | 0.63 |
| 86 | 100 | 0 | 0.63 |
| 105 | Stop | Stop | Stop |

Figure 5A:
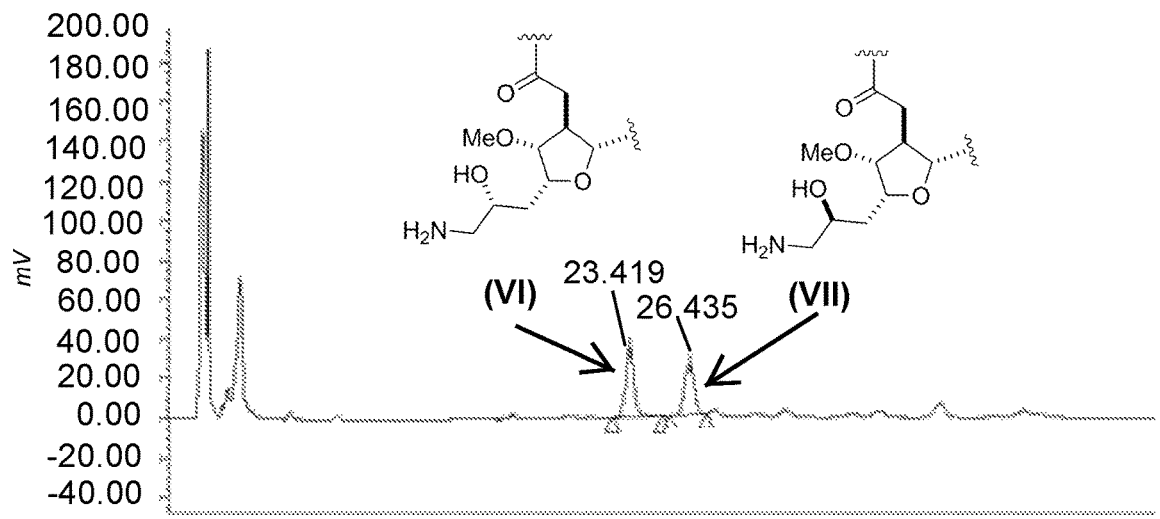
FIG. 5A is a chromatogram obtained from HPLC analysis of product obtained by the reaction of equimolar quantities of compound (II) and nitromethane using a tandem nitro aldol/reduction process as described in Example 4. Eribulin was separated from its C34 diastereomer by this process.
Figure 5B:
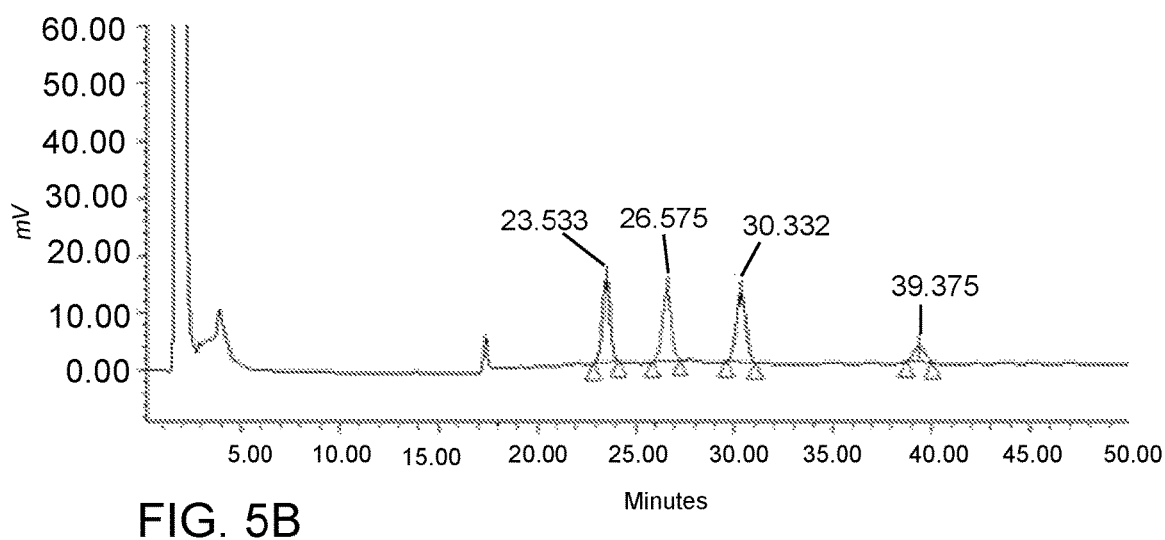
FIG. 5B is a chromatogram obtained from HPLC analysis of product obtained by the reaction of compound (II) with 0.2 molar equivalents of nitromethane using a tandem nitro aldol/reduction process as described in Example 4. Eribulin was separated from its C34 diastereomer by this process.

Sample chromatograms obtained from RP-HPLC purification are shown in FIG. 5A (one-pot process, 1:1 aldehyde:nitromethane by mole) and FIG. 5B (one-pot process, 5:1 aldehyde:nitromethane by mole).

Example 7. Purification of Compound of Formula (I) by Silica Gel Chromatography Crude compound of formula (I) (mixture of diastereomers, prepared using the one-pot procedure as described in Example 4) was purified by silica gel column chromatography (230-400 $SiO_2$, 0.5 cm d×5.5 cm h). Compound of formula (I) was eluted with 25 mL each of 3:2 heptane:ethyl acetate and ethyl acetate, 40 mL of 4:1 acetonitrile:water containing 0.2% $NH_4OH$. The silica column was conditioned with 3:2 heptane:ethyl acetate and crude product mixture was loaded with dichloromethane/heptane. The heptane:ethyl acetate and ethyl acetate eluants were collected in one fraction each (fractions 1 and 2). The acetonitrile:water eluant was collected in 4×10 mL fractions (fractions 3-6). Each fraction was subsequently analyzed by TLC and LC/MS. Fraction 4 was concentrated to provide a 1:1 mixture of eribulin and its C-34 diastereomer (2.5 mg, 3.56 μmol, 83% based on nitromethane, contained minor amide impurity).

Example 8. Synthesis of Compound of Formula (I) Via Cyanohydrin

Compound of formula (II) (78 m g, 0.112 mmol) was dissolved in (EtOAc:THF:AcOH:water; 2:1:1.6:0.4 (v/v), 25 V). Potassium cyanide (25 mg, 0.384 mmol) in water (0.17 mL) was added, and the solution stirred at room temperature and monitored by TLC (4:1 toluene/acetonitrile) and LCMS. When the reaction was deemed complete, water (20 mL) was added, and the reaction was stirred. The organic layer was removed, and the aqueous layer was extracted with EtOAc (3×15 mL). The combined extracts were washed with 10% aqueous sodium bicarbonate (20 mL). The aqueous layer was back-extracted with DCM (10 mL). The combined organic layers were concentrated and azeotroped with toluene to provide crude product diastereomers of formula (IV). The residue was purified by flash chromatography (6:1 to 4:1 toluene/acetonitrile) to provide the β-isomer (4 mg) and mixture of α-(epi-34) and β-isomers (19 mg).

A stock solution of tris(perfluorophenyl)borane and triethylsilane was prepared by dissolving tris(perfluorophenyl)borane (10.6 mg) and triethylsilane (0.275 mL) in D-chloroform (0.75 mL). 70 μL reagent solution (10 eq. silane, 0.03 eq. tris(perfluorophenyl)borane) were added to the α-isomer (5.00 mg, 6.888 μmol) at room temperature, and the reaction was monitored by LCMS. After 10 minutes, HCl (0.01 N, 0.2 mL) was added, and the reaction was stirred for 5 minutes. The reaction mixture was extracted with DCM (0.2 mL) to remove lipophilic impurities. The aqueous layer was treated with sodium bicarbonate (0.5 mL) and then extracted with DCM (2×0.4 mL). The combined extracts were concentrated to provide the compound of formula (I) (epi-34 eribulin).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of synthesizing a compound according to formula (I):

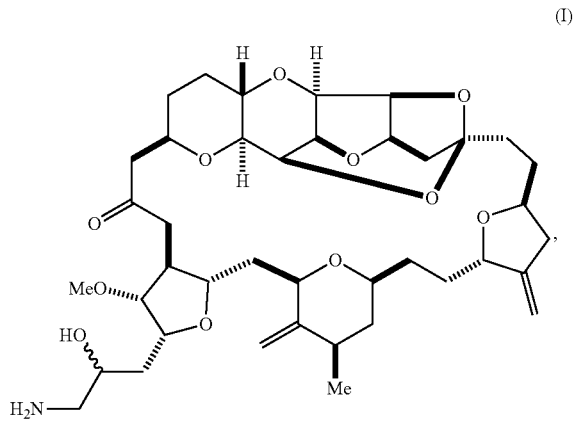

(I)

or a pharmaceutically acceptable salt thereof, the method comprising reacting an aldehyde according to formula (II):

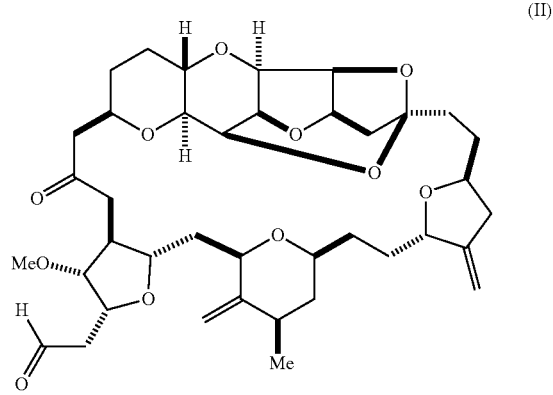

(II)

with nitromethane under Henry reaction conditions to form a compound according to formula (III):

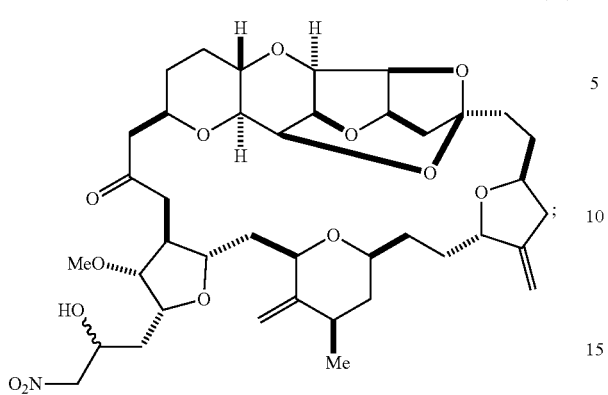

and reducing the compound according to formula (III) with a reducing agent to form the compound according to formula (I).

2. The method of claim 1, further comprising adding a base to a mixture comprising the aldehyde and the nitromethane.

3. The method of claim 2, wherein the base is sodium hydroxide.

4. The method of claim 1, wherein the reducing agent is a lanthanide salt.

5. The method of claim 4, wherein the lanthanide salt is samarium (II) iodide.

6. A method of synthesizing a compound according to formula (I):

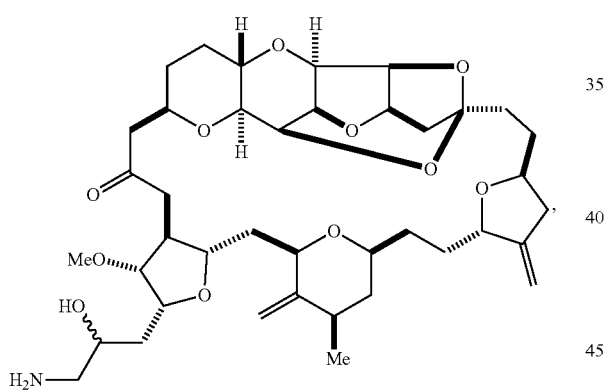

or a pharmaceutically acceptable salt thereof, the method comprising reacting an aldehyde according to formula (II):

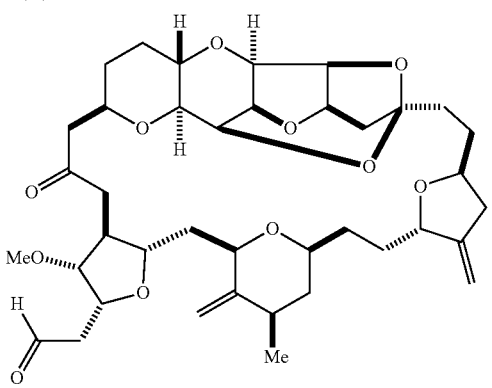

with a cyanide salt under conditions to form a cyanohydrin according to formula (IV):

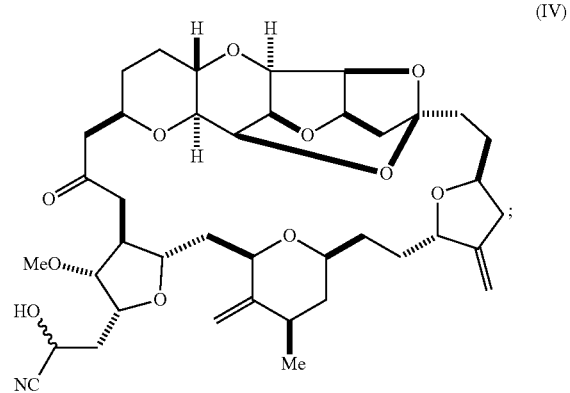

and reducing the cyanohydrin according to formula (IV) with a reducing agent to form the compound according to formula (I).

7. The method of claim 6, wherein the cyanide salt is potassium cyanide.

8. The method of claim 6, wherein the reducing agent is diethylsilane or triethylsilane.

9. The method of claim 6, further comprising adding a Lewis acid to a mixture of the cyanohydrin and the reducing agent.

10. The method of claim 9, wherein the Lewis acid is tris(perfluorophenyl)borane.

11. The method of claim 1, further comprising synthesizing the aldehyde according to formula (II) by reacting a diol according to formula (V):

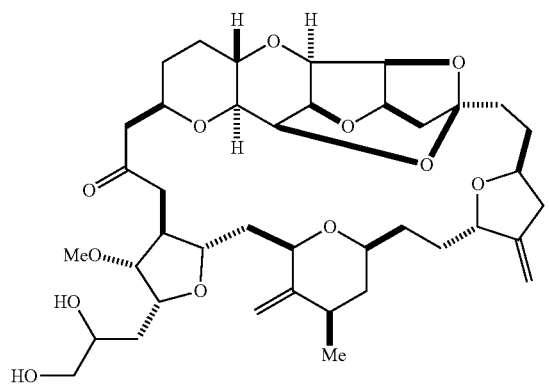

with an oxidizing agent to form the aldehyde.

12. The method of claim 11, wherein the oxidizing agent is sodium periodate.

13. The method of claim 1, further comprising salifying the compound of formula (I) to produce a pharmaceutically acceptable salt thereof.

14. The method of claim 13, wherein the pharmaceutically acceptable salt is the mesylate salt.

15. The method of claim 6, further comprising synthesizing the aldehyde according to formula (II) by reacting a diol according to formula (V):

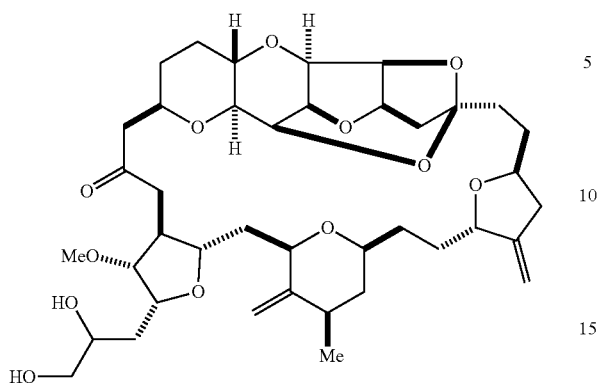
with an oxidizing agent to form the aldehyde.
16. The method of claim 15, wherein the oxidizing agent is sodium periodate.
17. The method of claim 6, further comprising salifying the compound of formula (I) to produce a pharmaceutically acceptable salt thereof.
18. The method of claim 17, wherein the pharmaceutically acceptable salt is the mesylate salt.
* * * * *